US012653876B2

(12) United States Patent
Wilson et al.

(10) Patent No.: US 12,653,876 B2
(45) Date of Patent: Jun. 16, 2026

(54) M HYO MULTIVALENT VACCINE AND USES THEREOF

(71) Applicant: BOEHRINGER INGELHEIM ANIMAL HEALTH USA INC., Duluth, GA (US)

(72) Inventors: Keith Wilson, Alexandria, MN (US); Paulraj Lawrence, Arden Hills, MN (US)

(*) Notice: Subject to any disclaimer, the term of this patent is extended or adjusted under 35 U.S.C. 154(b) by 0 days.

(21) Appl. No.: 18/343,081

(22) Filed: Jun. 28, 2023

(65) Prior Publication Data

US 2024/0024448 A1     Jan. 25, 2024

Related U.S. Application Data

(63) Continuation of application No. 15/378,165, filed on Dec. 14, 2016, now abandoned.

(60) Provisional application No. 62/272,017, filed on Dec. 28, 2015.

(51) Int. Cl.
| | |
|---|---|
| *A61K 39/02* | (2006.01) |
| *A61K 39/00* | (2006.01) |
| *A61K 39/12* | (2006.01) |
| *C12N 7/00* | (2006.01) |

(52) U.S. Cl.
CPC .......... *A61K 39/0241* (2013.01); *A61K 39/12* (2013.01); *C12N 7/00* (2013.01); *A61K 2039/5252* (2013.01); *A61K 2039/545* (2013.01); *A61K 2039/552* (2013.01); *A61K 2039/55505* (2013.01); *A61K 2039/55566* (2013.01); *A61K 2039/70* (2013.01); *C12N 2750/10011* (2013.01); *C12N 2750/10034* (2013.01); *C12N 2770/10034* (2013.01)

(58) Field of Classification Search
None
See application file for complete search history.

(56) References Cited

U.S. PATENT DOCUMENTS

| | | | |
|---|---|---|---|
| 3,917,819 | A | 11/1975 | Yoshioka et al. |
| 6,537,552 | B1 | 3/2003 | Minion et al. |
| 6,825,036 | B2 | 11/2004 | Makizumi et al. |
| 7,018,638 | B2 | 3/2006 | Chu et al. |
| 7,169,394 | B2 | 1/2007 | Chu et al. |
| 7,381,414 | B2 | 6/2008 | Lin et al. |
| 7,622,124 | B2 | 11/2009 | Chu et al. |
| 7,666,439 | B2 | 2/2010 | Chu et al. |
| 7,959,927 | B2 | 6/2011 | Chu et al. |
| 8,187,588 | B2 | 5/2012 | Chu et al. |
| 8,444,989 | B1 | 5/2013 | Ohnesorge et al. |
| 8,852,613 | B2 | 10/2014 | Ohnesorge et al. |
| 9,273,281 | B2 | 3/2016 | Jordan et al. |
| 9,650,600 | B2 | 5/2017 | Galvin et al. |
| 9,650,601 | B2 | 5/2017 | Nitzel et al. |

| | | | |
|---|---|---|---|
| 9,662,385 | B2 | 5/2017 | Dominowski et al. |
| 9,878,027 | B2 | 1/2018 | Jordan et al. |
| 9,950,061 | B2 | 4/2018 | Hernandez et al. |
| 10,117,921 | B2 | 11/2018 | Dominowski et al. |
| 10,238,736 | B2 | 3/2019 | Dominowski et al. |
| 10,512,680 | B2 | 12/2019 | Jordan et al. |
| 10,758,602 | B2 | 9/2020 | Jordan et al. |
| 2003/0017171 | A1 | 1/2003 | Chu et al. |
| 2003/0064079 | A1 | 4/2003 | Goudie et al. |
| 2003/0109473 | A1 | 6/2003 | Keich et al. |
| 2005/0013823 | A1 | 1/2005 | Keich et al. |
| 2005/0037027 | A1 | 2/2005 | Lin et al. |
| 2007/0009545 | A1 | 1/2007 | Frey et al. |
| 2008/0268426 | A1 | 10/2008 | Murtaugh et al. |
| 2009/0042814 | A1 | 2/2009 | Petyaev et al. |
| 2009/0162398 | A1* | 6/2009 | Wu ......................... A61P 31/12 435/235.1 |
| 2011/0059126 | A1* | 3/2011 | Kohler .................... A61P 31/00 424/202.1 |
| 2011/0150770 | A1 | 6/2011 | Bautista et al. |
| 2012/0213816 | A1 | 8/2012 | Chu et al. |
| 2013/0052717 | A1 | 2/2013 | Liu et al. |
| 2013/0230558 | A1 | 9/2013 | Ohnesorge et al. |
| 2013/0266601 | A1 | 10/2013 | Galvin et al. |
| 2013/0266602 | A1 | 10/2013 | Nitzel et al. |
| 2013/0266603 | A1 | 10/2013 | Nitzel et al. |
| 2014/0023681 | A1 | 1/2014 | Hause |
| 2014/0186393 | A1 | 7/2014 | Jordan et al. |
| 2014/0186394 | A1 | 7/2014 | Jordan et al. |

(Continued)

FOREIGN PATENT DOCUMENTS

| | | |
|---|---|---|
| CA | 2793141 A1 | 10/2011 |
| CN | 102258776 A | 11/2011 |

(Continued)

OTHER PUBLICATIONS

Boettcher et al. Journal of Swine Health and Production vol. 10, No. 6 2002 (Year: 2002).*
Allan et al., 1998, Eur. J. Vet. Diagn. Investig. 10, 3-10, "Isolation of porcine circovirus-like viruses from pigs with a wasting disease in the USA and Europe".
Allen et al., 1999, Journal of Comparative Pathology, 1999, 121(1), pl-11, "Experimental reproduction of severe wasting disease by co-infection of pigs with porcine circovirus and porcine parvovirus".
Ellis et al., 1998, Can. Vet. J. 39, 44-51, "Isolation of circovirus from lesions of pigs with postweaning multisystemic wasting syndrome".

(Continued)

*Primary Examiner* — Jana A Hines
*Assistant Examiner* — Khatol S Shahnan Shah
(74) *Attorney, Agent, or Firm* — Shanyun Lu

(57)     ABSTRACT

The present invention relates to compositions or vaccines for combating *Mycoplasma hyopneumoniae* (*M hyo*), Porcine Circovirus type 2 (PCV2), and Porcine Reproductive and Respiratory Syndrome Virus (PRRSV) infections in animals and for increasing the ability of pigs to gain weight and/or improve death loss, methods of vaccination against the infections, and kits for use with such methods and compositions.

7 Claims, 9 Drawing Sheets

Specification includes a Sequence Listing.

(56) References Cited

U.S. PATENT DOCUMENTS

| | | | |
|---|---|---|---|
| 2014/0271698 A1* | 9/2014 | Jordan | A61P 37/04 |
| | | | 435/235.1 |
| 2014/0370058 A1 | 12/2014 | Ohnesorge et al. | |
| 2015/0283229 A1 | 10/2015 | Hernandez et al. | |
| 2016/0136254 A1 | 5/2016 | Jordan et al. | |
| 2018/0125957 A1 | 5/2018 | Jordan et al. | |
| 2018/0207260 A1 | 7/2018 | Hernandez et al. | |
| 2019/0038737 A1 | 2/2019 | Dominowski et al. | |

FOREIGN PATENT DOCUMENTS

| | | | |
|---|---|---|---|
| CN | 104043118 A | 9/2014 | |
| EP | 1260581 A1 | 11/2002 | |
| EP | 1862537 A1 | 12/2007 | |
| GB | 1074920 A | 7/1967 | |
| GB | 1137306 A | 12/1968 | |
| GB | 1439407 A | 6/1976 | |
| JP | H11507225 A | 6/1999 | |
| JP | 2001278808 A | 10/2001 | |
| WO | 1993016726 A2 | 9/1993 | |
| WO | 1996039629 A1 | 12/1996 | |
| WO | 2001064846 A1 | 9/2001 | |
| WO | 2002049666 A2 | 6/2002 | |
| WO | 2003004052 A1 | 1/2003 | |
| WO | 2003017755 A2 | 3/2003 | |
| WO | 2006056841 A1 | 6/2006 | |
| WO | 2006095431 A1 | 9/2006 | |
| WO | 2007103042 A2 | 9/2007 | |
| WO | 2007116032 A1 | 10/2007 | |
| WO | 2009036241 A1 | 3/2009 | |
| WO | 2009058833 A2 | 5/2009 | |
| WO | 2009061798 A1 | 5/2009 | |
| WO | 2009126356 A2 | 10/2009 | |
| WO | 2009142086 A1 | 11/2009 | |
| WO | 2009156960 A2 | 12/2009 | |
| WO | 2010051210 A1 | 5/2010 | |
| WO | 2010132932 A1 | 11/2010 | |
| WO | 2011075379 A1 | 6/2011 | |
| WO | 2011124653 A1 | 10/2011 | |
| WO | 2013152081 A1 | 10/2013 | |
| WO | 2013152083 A2 | 10/2013 | |
| WO | 2014105671 A1 | 7/2014 | |
| WO | 2014105672 A1 | 7/2014 | |

OTHER PUBLICATIONS

Johnson et al., 2011, J of Gen Virol. 92(5), pp. 1107-1116, "Novel structural protein in porcine reproductive and respiratory syndrome virus encoded by an alternative ORF5 present in all arteriviuses".

Kobisch & Friis, 1996, Rev Sci Tech. 15(4):1569-605, "Swine mycoplasmoses".

Lee and Yoo, 2005, J Gen Virol. 86(11):3091-6, "Cysteine residues of the porcine reproductive and respiratory syndrome virus small envelope protein are non-essential for virus infectivity".

Maes et al., 1996, Vet Q. 18(3):104-9, "Enzootic pneumonia in pigs".

Meulenberg et al., 1993, Virology. 192(1):62-72, "Lelystad virus, the causative agent of porcine epidemic abortion nd respiratory syndrome (PEARS), is related to LDV and EAV".

Morozov et al., 1998, J. Clin. Microbial. 36, 2535-2541, "Detection of a novel strain of porcine circovirus in pigs with postweaning multisystemic wasting syndrome".

Thacker, 2004, Anim Health Res Rev. Dec. 2004;5(2):317-20, "Diagnosis of Mycoplasma hyopneumoniae".

Thacker, 2001, Vet Clin North Am Food Anim Pract. 17(3):551-65, "Immunology of the porcine respiratory disease complex".

Papatsiros, V.G., "Impact of a killed PRRSV vaccine on sow longevity in a PRRSV infected swine herd", J. Appl. Animal Res, 40/4, pp. 297-306, 2012.

Xie, Yiwen, et al. "Immune interference in effectiveness of influenza and COVID-19 vaccination." Frontiers in Immunology 14 (2023): 1167214.

Abstract and Claims in English for CN102258776B, 2011.

Abstract in English for JP2001278808A, 2001.

Abstract in English for WO2009142086A1, 2009.

Bhogal et al., "Production of mycoplasma-specific antisera in rabbits immunologically tolerized at birth to mycoplasma medium constituents." Journal of Immunological Methods 97.2 (1987): 191-199.

Declaration Brain Thomas Martinson + Appendices: CV Brian Thomas Martinson; Safety Data Sheet for Ingelvac MycoMAX; Data form Clinical studies; Material Safety Data Sheet for Ingelvac Mycoflex; USDA Veterinary Service Memorandum 800.202.

Draganov et al., "Mccoy and Mccoy-Plovdiv Cell Lines in Experimental and Diagnostic Practice—Past, Present and Perspectives." Journal of Culture Collections 4.1 (2004-2005): 3-16.

Gaush et al., "Characterization of an Established Line of Canine Kidney Cells (MDCK)." Proceedings of the Society for Experimental Biology & Medicine 122.3 (1966): 931-935.

Gregersen, Jens-Peter. "A quantitative risk assessment of exposure to adventitious agents in a cell culture-derived subunit influenza vaccine." Vaccine 26.26 (2008): 3332-3340.

Imura et al., "An Immunoelectron Microscopic Study of Mycoplasma Hyosynoviae in Primary Swine Kiney Cell Culture." Kobe Journal of Medical Sciences 29.1 (1983): 1-15.

Kim et al., "Comparative efficacy of commercial Mycoplasma hyopneumoniae and porcine circovirus 2 (PCV2) vaccines in pigs experimentally infected with M. hyopneumoniae and PCV2." Vaccine 29.17 (2011): 3206-3212.

Kobayashi et al., "Marolide Susceptibility of Mycoplasma hyorhinis Isolated from Piglets." Antimicrobial Agents and Chemotherapy 40.4 (1996): 1030-1032.

Kotani, Hitoshi, et al. "Rapid and simple identification of mycoplasmas by immunobinding." Journal of immunological methods 85.2 (1985): 257-267.

Lauritsen, Klara Tølbøl, et al. "Testing immunogenicity of Mycoplasma hyosynoviae vaccine candidates: Induction of antibodies and IFN-gamma response." Veterinary Immunology and Immunopathology 128 (2009): 329.

Mochizuki, Masami, "Growth characteristics of canine pathogenic viruses in MDCK cells cultured in RPMI 1640 medium without animal protein." Vaccine . 11 (2006): 1744-1748.

Neyrolles et al., "Identification of two glycosylated components of Mycoplasma penetrans: a surface-exposed capsular polysaccharide and a glycolipid fraction." Microbiology 144.5 (1998): 1247-1255.

Okada et al., "Cytological and immunological changes in bronchoalveolar lavage fluid and histological observation of lung lesions in pigs immunized with Mycoplasma hyopneumoniae inactivated vaccine prepared from broth culture supernate." Vaccine 18.25 (2000): 2825-2831.

Pfizer Animal Health, "RespiSure1ONE: From Day 1, RespiSure-ONE® offers more flexibility and the start of exceptional M. hyopneumoniae protection." (2010): 1-2. [Accessed at https://www.zoetisus.com/_locale-assets/mcm-portal-assets/my-resources/respisureoneproductsheet.pdf on Dec. 15, 2017].

Potgieter et al., "Chronological Development of Mycoplasma hyorhinis and Mycoplasma hyosynoviae Infections in Cultures of a Swine Synovial Cell Strain." Canadian Journal of Comparative Medicine-Revue Canadienne Demedecine Comparee 36.2 (1972): 145-149.

Sobko et al., "Development of Scientific Techniques for the Prevention of Mycoplasma Infections in Swine." Archiv Fuer Experimentelle Veterinaermedizin 43.5 (1989): 645-655. (Abstract in English on p. 654).

USDA Product Licensure 124-2775.02, Jul. 24, 2019.

USDA Product Licensure 124-27H8.00; Jan. 19, 2018.

Volokhov, Dmitriy V., et al. "Biological enrichment of Mycoplasma agents by cocultivation with permissive cell cultures." Applied and environmental microbiology 74.17 (2008): 5383-5391.

Volokhov, Dmitriy V., et al. "Mycoplasma testing of cell substrates and biologics: review of alternative non-microbiological techniques." Molecular and cellular probes 25.2-3 (2011): 69-77.

Written Opinion for PCT/US2013/076803 mailed May 27, 2014.

Written Opinion for PCT/US2013/076807 mailed Mar. 18, 2014.

Xiong, Qi-yan, et al. "Immune Study of a Intramuscular Injected Live Vaccine against Mycoplasma hyopneumoniae Enhanced by

(56) References Cited

OTHER PUBLICATIONS

Different Adjuvants." China Animal Husbandry & Veterinary Medicine 38.10 (2011): 163-168. (Abstract in English on p. 168).

Zhang et al., "Research advance in vaccines against important mycoplasmal diseases in livestock." Chinese Veterinary Science 41.12 (2011): 1314-1320. (Abstract in English on p. 1314).

Allison, A. C., and Gregory Gregoriadis. "Liposomes as immunological adjuvants." Nature 252.5480 (1974): 252-252.

Calcutt, Michael J., et al. "Genome sequence of Mycoplasma hyorhinis strain GDL-1." Journal of Bacteriology 194.7 (2012): 1848-1848.

Chambaud, Isabelle, et al. "The complete genome sequence of the murine respiratory pathogen Mycoplasma pulmonis." Nucleic acids research 29.10 (2001): 2145-2153.

Dancey, George F., Tatsuji Yasuda, and Stephen C. Kinsky. "Effect of liposomal model membrane composition on immunogenicity." The Journal of Immunology 120.4 (1978): 1109-1113.

Extended European Search Report for European Application No. 20160539.1, dated Feb. 24, 2021, 52 Pages.

Fraser, Claire M., et al. "The minimal gene complement of Mycoplasma genitalium." Science 270.5235 (1995): 397-404.

International Search Report and Written Opinion for International Application No. PCT/US2013/076803, dated May 27, 2014, 31 Pages.

International Search Report and Written Opinion for International Application No. PCT/US2016/066481, dated Jun. 19, 2017, 17 Pages.

International Search Report for International Application No. PCT/US2013/076807, dated Mar. 27, 2014, 4 Pages.

Liu, Wei, et al. "Complete genome sequence of Mycoplasma hyorhinis strain HUB-1." Journal of bacteriology 192.21 (2010): 5844-5845.

Maes, Dominiek, et al. "Control of Mycoplasma hyopneumoniae infections in pigs." Veterinary microbiology 126.4 (2008): 297-309.

Simionatto, Simone, et al. "Mycoplasma hyopneumoniae: from disease to vaccine development." Veterinary Microbiology 165.3-4 (2013): 234-242.

Todd, C. W., et al. "Development of an adjuvant-active nonionic block copolymer for use in oil-free subunit vaccines formulations." Vaccine 15.5 (1997): 564-570.

* cited by examiner qPCR performed on serum drawn on the first day of the study

FFN Titers from serum drawn on days 0 and 21

(*) indicates group that had significantly higher titers based on the results of a Student's t-test ($\alpha=0.05$)

Comparing rate of gain amongst all groups

Mean weight of groups at days 0 and 61 of the study

Connecting letter report describes the results of at Student's t-test (α=0.05)

Comparison of finishing weights based on Mycoplasma Vaccination Status p-value indicates the result of a two-way ANOVA

Figure 6

| SEQ ID NO: | Type | Gene Description |
|---|---|---|
| 1 | DNA | DNA sequence for ORF5 of PRRSV strain, isolate 14-02227-1 |
| 2 | protein | Protein sequence for ORF5 of PRRSV strain, isolate 14-02227-1 |
| 3 | protein | Protein sequence for ORF5 of PRRSV strain, isolate 14-02094-1 |
| 4 | protein | Protein sequence for ORF5 of PRRSV strain, isolate S11-1118-1 |
| 5 | protein | Protein sequence for ORF5 of PRRSV strain, reference isolate |
| 6 | protein | Protein sequence for ORF5 of PRRSV strain, PRRSV Ref. Pfizer Fostera |
| 7 | protein | Protein sequence for ORF5 of PRRSV strain, RespPRRS-BI Ingelvac MLV |
| 8 | protein | Protein sequence for ORF5 of PRRSV strain, PRRS-BI Ingelvac ATP |
| 9 | protein | Protein sequence for ORF5 of PRRSV strain, *EURO PRRS Strain Lelystad strain |

Figure 7A

SEQ ID NO:1  (DNA sequence of ORF5 PRRSV 603bp)
ATGTTGGGGAAATGCTTGACCGCGGGCTGCTGCTCGCAATTGCCTTTTTTGTGGTGTATCGTGCCGTTCT
GTTTTGTTGCGCTCGTCAACGCCAACAACAGCAGCAGCTCCCATTTACAGTTGATTTATAACCTGACGAT
ATGTGAGCTGAATGGCACAGATTGGCTAAACAAAAGTTTTGATTGGGCGGTGGAGACCTTTGTTATTTTT
CCTGTGTTGACTCATATTGTCTCCTATGGCGCCCTCACCACCAGCCATTTCCTTGACACAGTCGGCCTGA
TCACCGTGTCTGCCGCCGGATATTACCACGGGCGGTATGTCTTGAGTAGCATTTATGCCGTCTGCGCCCT
GGCTGCGTTAACTTGCTTCGTCATCAGGCTAACAAAAAATTGTATGTCCTGGCGTTACTCATGCACCAGA
TATACTAATTTTCTTCTGGACACCAAGGGCAAACTCTATCGTTGGCGGTCTCCTGTCATCATAGAGAAAG
GGGGTAAAATTGAGGTCGAAGGTCACCTGATCGACCTCAAGAGAGTTGTGCTTGACGGTTCCGCGGCAAC
CCCTGTAACCAAAGTTTCAGCGGAACAATGGGGCCGTCCT SEQ ID NO:2  (ORF5 PRRSV 200aa, isolate 14-02227-1)
MLGKCLTAGCCSQLPFLWCIVPFCFVALVNANNSSSSHLQLIYNLTICELNGTDWLNKSFDWAVETFVIF
PVLTHIVSYGALTTSHFLDTVGLITVSAAGYYHGRYVLSSIYAVCALAALTCFVIRLTKNCMSWRYSCTR
YTNFLLDTKGKLYRWRSPVIIEKGGKIEVEGHLIDLKRVVLDGSAATPVTKVSAEQWGRP SEQ ID NO:3  isolate 14-02094-1
MLGKCLTAGCCSQLPFLWCIVPFCFVALVNANNSSSSHLQLIYNLTICELNGTDWLNKSFDWAVETFVIFP
VLTHIVSYGALTTSHFLDTVGLITVSAAGYYHGRYVLSSIYAVCALAALTCFVIRLTKNCMSWRYSCTRYT
NFLLDTKGKLYRWRSPVIIEKGGKIEVEGHLIDLKRVVLDGSAATPVTKVSAEQWGRP SEQ ID NO:4   isolate S11-1118-1
MLGKCLTAGYCSQLPFLWCIVPFCFAALVNANSNSSSHLQLIYNLTICELNGTDWLNNKFDWAVETFVIFP
VLTHIVSYGALTTSHLLDTVGLITVSTAGYCHGRYVLSSIYAVCALAALICFAIRLAKNCMSWRYSCTRYT
NFLLDTKGKLYRWRSPVIIEKGGKVDVGGHLIDLKRVVLDGSAATPVTKISAEQWGRP SEQ ID NO:5  reference isolate
MLGKCLTAGCCSQLPSLWCIVPFCFAALVNANSSSSSHLQLIYNLTLCELNGTDWLNNKFDWAVETFVIFP
VLTHIVSYGALTTSHFLDTVGLITVSTAGFYHGRYVLSSIYAVCALAALTCFVIRLAKNCMSWRYSCTRYT
NFLLDTKGRLYRWRSPVIIEKGGKVEVEGHLIDLKRVVLDGSAATPVTRVSAEQWGRP SEQ ID NO:6  PRRSV ref. isolate Fostera
MLGKCLTAGCCSRLLSLWCIVPFWFAVLGNANSSSSSHFQLIYNLTLCELNGTDWLAEKFDWAVETFVIFP
VLTHIVSYCALTTSHFLDTVGLVTVSTAGFYHGRYVLSSIYAVCALAALICFVIRLAKNCMSWRYSCTRYT
NFLLDTKGRLYRWRSPVIIEKRGKVEVEGHLIDLKRVVLDGSVATPLTRVSAEQWGRL SEQ ID NO:7  RespPRRS-BI Ingelvac MLV
MLEKCLTAGCCSQLLSLWCIVPFCFAVLANASNDSSSHLQLIYNLTLCELNGTDWLANKFDWAVESFVIFP
VLTHIVSYGALTTSHFLDTVALVTVSTAGFVHGRYVLSSIYAVCALAALTCFVIRFAKNCMSWRYACTRYT
NFLLDTKGGLYRWRSPVIIEKRGKVEVEGHLIDLKRVVLDGSVATPITRVSAEQWGRP SEQ ID NO:8   PRRS-BI Ingelvac ATP
MLGRGVTGGCGSRTLSVWCIVPFCFAALVNANSNSSSHLQLIYNLTLCELNGTDWLKNKFDWALETFVIFP
VLTHIVSYSALTTSHFLDTVGLVTVSTAGFYHGRYVLSSIYAVCALAALTCFVIRLAKNCMSWRYSCTRYT
NFLLDTKGRLYRWRSPVIIEKGGKVEVEGHLIDLKRVVLDGSVATPLTRVSAEQWGRP

Figure 7B

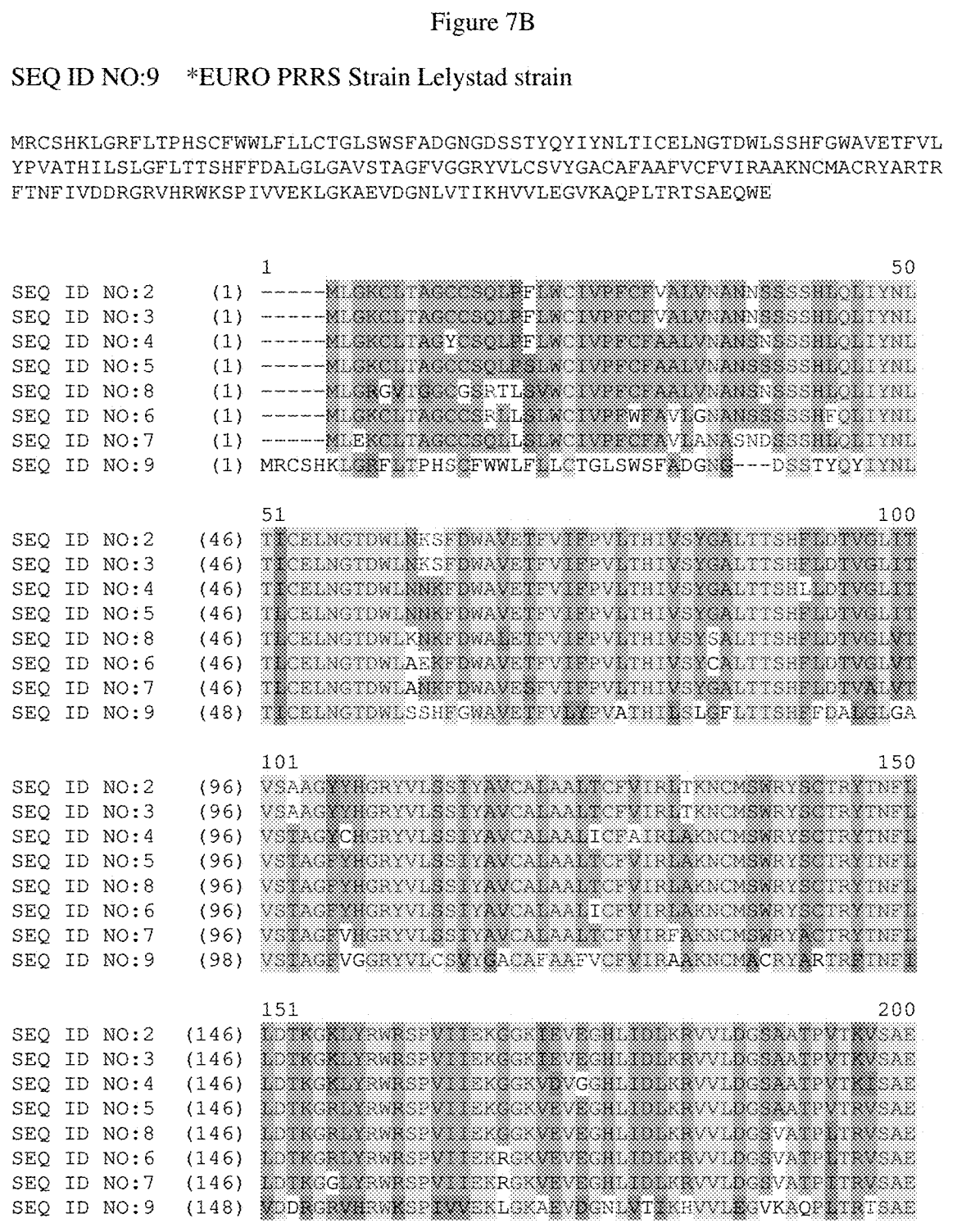

SEQ ID NO:9    *EURO PRRS Strain Lelystad strain

MRCSHKLGRFLTPHSCFWWLFLLCTGLSWSFADGNGDSSTYQYIYNLTICELNGTDWLSSHFGWAVETFVL
YPVATHILSLGFLTTSHFFDALGLGAVSTAGFVGGRYVLCSVYGACAFAAFVCFVIRAAKNCMACRYARTR
FTNFIVDDRGRVHRWKSPIVVEKLGKAEVDGNLVTIKHVVLEGVKAQPLTRTSAEQWE

```
                         201
SEQ ID NO:2  (196)  QWGRI
SEQ ID NO:3  (196)  QWGRI
SEQ ID NO:4  (196)  QWGRI
SEQ ID NO:5  (196)  QWGRI
SEQ ID NO:8  (196)  QWGRI
SEQ ID NO:6  (196)  QWGRL
SEQ ID NO:7  (196)  QWGRI
SEQ ID NO:9  (198)  QWE--
```

Sequence identity percentage

| SEQ ID NO: | 2 | 3 | 4 | 5 | 6 | 7 | 8 | 9 |
|---|---|---|---|---|---|---|---|---|
| 2 | 100% | 100% | 92.0% | 94.0% | 87.0% | 86.5% | 86.0% | 53.7% |
| 3 | | 100% | 92.0% | 94.0% | 87.0% | 86.5% | 86.0% | 53.7% |
| 4 | | | 100% | 93.0% | 86.5% | 85.5% | 86.0% | 53.2% |
| 5 | | | | 100% | 92.5% | 91.0% | 92.0% | 55.1% |
| 6 | | | | | 100% | 90.5% | 90.5% | 56.1% |
| 7 | | | | | | 100% | 87.5% | 54.1% |
| 8 | | | | | | | 100% | 53.0% |
| 9 | | | | | | | | 100% |

Phylogenetic tree

SEQ ID NO:2 (0.0000)
SEQ ID NO:3 (0.0000)
SEQ ID NO:4 (0.0430)
SEQ ID NO:5 (0.0093)
SEQ ID NO:8 (0.0554)
SEQ ID NO:6 (0.0372)
SEQ ID NO:7 (0.0578)
SEQ ID NO:9 (0.3705)

```
                    SEQUENCE LISTING

Sequence total quantity: 9
SEQ ID NO: 1            moltype = DNA  length = 600
FEATURE                 Location/Qualifiers
misc_feature            1..600
                        note = DNA sequence of ORF5 PRRSV
source                  1..600
                        mol_type = other DNA
                        organism = synthetic construct
SEQUENCE: 1
atgttgggga aatgcttgac cgcgggctgc tgctcgcaat tgcctttttt gtggtgtatc   60
gtgccgttct gttttgttgc gctcgtcaac gccaacaaca gcagcagctc ccatttacag  120
ttgatttata acctgacgat atgtgagctg aatggcacag attggctaaa caaaagtttt  180
gattgggcgg tggagacctt tgttattttt cctgtgttga ctcatattgt ctcctatggc  240
gccctcacca ccagccattt ccttgacaca gtcggcctga tcaccgtgtc tgccgccgga  300
tattaccacg ggcggtatgt cttgagtagc atttatgccg tctgcgccct ggctgcgtta  360
acttgcttcg tcatcaggct aacaaaaaat tgtatgtcct ggcgttactc atgccaccaga  420
tatactaatt ttcttctgga caccaagggc aaactctatc gttggcggtc tcctgtcatc  480
atagagaaag ggggtaaaat tgaggtcgaa ggtcacctga tcgacctcaa gagagttgtg  540
cttgacggtt ccgcggcaac ccctgtaacc aaagtttcag cggaacaatg gggccgtcct  600

SEQ ID NO: 2            moltype = AA  length = 200
FEATURE                 Location/Qualifiers
REGION                  1..200
                        note = ORF5 PRRSV isolate 14-02227-1
source                  1..200
                        mol_type = protein
                        organism = synthetic construct
SEQUENCE: 2
MLGKCLTAGC CSQLPFLWCI VPFCFVALVN ANNSSSSHLQ LIYNLTICEL NGTDWLNKSF   60
DWAVETFVIF PVLTHIVSYG ALTTSHFLDT VGLITVSAAG YYHGRYVLSS IYAVCALAAL  120
TCFVIRLTKN CMSWRYSCTR YTNFLLDTKG KLYRWRSPVI IEKGGKIEVE GHLIDLKRVV  180
LDGSAATPVT KVSAEQWGRP                                              200

SEQ ID NO: 3            moltype = AA  length = 200
FEATURE                 Location/Qualifiers
```

-continued

```
REGION                  1..200
                        note = ORF5 PRRSV isolate 14-02094-1
source                  1..200
                        mol_type = protein
                        organism = synthetic construct
SEQUENCE: 3
MLGKCLTAGC CSQLPFLWCI VPFCFVALVN ANNSSSSHLQ LIYNLTICEL NGTDWLNKSF    60
DWAVETFVIF PVLTHIVSYG ALTTSHFLDT VGLITVSAAG YYHGRYVLSS IYAVCALAAL   120
TCFVIRLTKN CMSWRYSCTR YTNFLLDTKG KLYRWRSPVI IEKGGKIEVE GHLIDLKRVV   180
LDGSAATPVT KVSAEQWGRP                                               200

SEQ ID NO: 4            moltype = AA   length = 200
FEATURE                 Location/Qualifiers
REGION                  1..200
                        note = ORF5 PRRSV isolate S11-1118-1
source                  1..200
                        mol_type = protein
                        organism = synthetic construct
SEQUENCE: 4
MLGKCLTAGY CSQLPFLWCI VPFCFAALVN ANSNSSSHLQ LIYNLTICEL NGTDWLNNKF    60
DWAVETFVIF PVLTHIVSYG ALTTSHLLDT VGLITVSTAG YCHGRYVLSS IYAVCALAAL   120
ICFAIRLAKN CMSWRYSCTR YTNFLLDTKG KLYRWRSPVI IEKGGKVDVG GHLIDLKRVV   180
LDGSAATPVT KISAEQWGRP                                               200

SEQ ID NO: 5            moltype = AA   length = 200
FEATURE                 Location/Qualifiers
REGION                  1..200
                        note = ORF5 PRRSV reference isolate
source                  1..200
                        mol_type = protein
                        organism = synthetic construct
SEQUENCE: 5
MLGKCLTAGC CSQLPSLWCI VPFCFAALVN ANSSSSSHLQ LIYNLTLCEL NGTDWLNNKF    60
DWAVETFVIF PVLTHIVSYG ALTTSHFLDT VGLITVSTAG FYHGRYVLSS IYAVCALAAL   120
TCFVIRLAKN CMSWRYSCTR YTNFLLDTKG RLYRWRSPVI IEKGGKVEVE GHLIDLKRVV   180
LDGSAATPVT RVSAEQWGRP                                               200

SEQ ID NO: 6            moltype = AA   length = 200
FEATURE                 Location/Qualifiers
REGION                  1..200
                        note = ORF5 PRRSV ref. isolate Fostera
source                  1..200
                        mol_type = protein
                        organism = synthetic construct
SEQUENCE: 6
MLGKCLTAGC CSRLLSLWCI VPFWFAVLGN ANSSSSSHFQ LIYNLTLCEL NGTDWLAEKF    60
DWAVETFVIF PVLTHIVSYC ALTTSHFLDT VGLVTVSTAG FYHGRYVLSS IYAVCALAAL   120
ICFVIRLAKN CMSWRYSCTR YTNFLLDTKG RLYRWRSPVI IEKRGKVEVE GHLIDLKRVV   180
LDGSVATPLT RVSAEQWGRL                                               200

SEQ ID NO: 7            moltype = AA   length = 200
FEATURE                 Location/Qualifiers
REGION                  1..200
                        note = ORF5 RespPRRS-BI Ingelvac MLV
source                  1..200
                        mol_type = protein
                        organism = synthetic construct
SEQUENCE: 7
MLEKCLTAGC CSQLLSLWCI VPFCFAVLAN ASNDSSSHLQ LIYNLTLCEL NGTDWLANKF    60
DWAVESFVIF PVLTHIVSYG ALTTSHFLDT VALVTVSTAG FVHGRYVLSS IYAVCALAAL   120
TCFVIRFAKN CMSWRYACTR YTNFLLDTKG GLYRWRSPVI IEKRGKVEVE GHLIDLKRVV   180
LDGSVATPIT RVSAEQWGRP                                               200

SEQ ID NO: 8            moltype = AA   length = 200
FEATURE                 Location/Qualifiers
REGION                  1..200
                        note = ORF5 PRRS-BI Ingelvac ATP
source                  1..200
                        mol_type = protein
                        organism = synthetic construct
SEQUENCE: 8
MLGRGVTGGC GSRTLSVWCI VPFCFAALVN ANSNSSSHLQ LIYNLTLCEL NGTDWLKNKF    60
DWALETFVIF PVLTHIVSYS ALTTSHFLDT VGLVTVSTAG FYHGRYVLSS IYAVCALAAL   120
TCFVIRLAKN CMSWRYSCTR YTNFLLDTKG RLYRWRSPVI IEKGGKVEVE GHLIDLKRVV   180
LDGSVATPLT RVSAEQWGRP                                               200

SEQ ID NO: 9            moltype = AA   length = 200
FEATURE                 Location/Qualifiers
REGION                  1..200
```

-continued

```
                            note = ORF5 EURO PRRS Strain Lelystad strain
source                      1..200
                            mol_type = protein
                            organism = synthetic construct
SEQUENCE: 9
MRCSHKLGRF LTPHSCFWWL FLLCTGLSWS FADGNGDSST YQYIYNLTIC ELNGTDWLSS   60
HFGWAVETFV LYPVATHILS LGFLTTSHFF DALGLGAVST AGFVGGRYVL CSVYGACAFA  120
AFVCFVIRAA KNCMACRYAR TRFTNFIVDD RGRVHRWKSP IVVEKLGKAE VDGNLVTIKH  180
VVLEGVKAQP LTRTSAEQWE                                             200
```

M HYO MULTIVALENT VACCINE AND USES THEREOF

CROSS-REFERENCE TO RELATED APPLICATIONS

This application is a continuation of U.S. patent application Ser. No. 15/378,165, filed Dec. 14, 2016; which claims priority to U.S. provisional application 62/272,017 filed on Dec. 28, 2015, the entire contents of which are hereby incorporated by reference herein.

STATEMENT REGARDING SEQUENCE LISTING

The Sequence Listing associated with this application is provided in XML format in lieu of a paper copy, and is hereby incorporated by reference into the specification. The name of the XML file containing the Sequence Listing is MER15-288-US-3_SL.xml. The XML file is 14,283 bytes; it was created on 29 Jun. 2023; and it is being submitted electronically via EFS-Web, concurrent with the filing of the specification.

FIELD OF THE INVENTION

The present invention relates to compositions or vaccines for combating *Mycoplasma hyopneumoniae* (*M hyo*), Porcine Circovirus type 2 (PCV2), and Porcine Reproductive and Respiratory Syndrome Virus (PRRSV) infections in animals and increasing the ability of pigs to gain weight or improve death loss, methods of vaccination against the infections, and kits for use with such methods and compositions.

BACKGROUND OF THE INVENTION

Circoviruses, the common name for a family of viruses named Circoviridae and that is found in a range of plant and animal species, are characterized as round, non-enveloped virions with mean diameters from 17 to 23.5 nm containing circular, single-stranded deoxyribonucleic acid (ssDNA). The ssDNA genome of the circoviruses represents the smallest viral DNA replicons known.

A variety of circoviruses have been identified in a range of animal species including PCV. PCV type II ("PCVII" or "PCV2"), in contrast to PCV type I ("PCVI" or "PCV1"), is closely associated with postweaning multisystemic wasting syndrome (PMWS) in weaning pigs (see Allan et al. Eur. J. Vet. Diagn. Investig. 1998, 10, 3-10; Ellis et al. Can. Vet. J. 1998, 39, 44-51 and Morozov et al. J. Clin. Microbiol. 1998, 36, 2535-2541). PCV2 has been recognized as the primary causative agent of PMWS, now known as PCVAD (porcine circovirus-associated disease) since the name was modified in March 2006 by the American Association of Swine Veterinarians (AASV). Pigs with naturally acquired or experimentally induced PCV2 infections present with progressive weight loss, tachypnea, dyspnea, and jaundice (Allan et al. 1998; Allan et al. 1999; Ellis et al. 1998; Ellis et al. 1999). Gross pathologic findings that have been directly associated with PCV2 antigen include, lymphadenopathy, interstitial pneumonia, hepatitis and nephritis (Allan et al. 1998; Allan et al. 1999; Ellis et al. 1998; Ellis et al. 1999).

*Mycoplasma hyopneumoniae*, the cause of enzootic pneumonia, remains an important pathogen in the swine industry. This small, complex organism colonizes the ciliated cells of the respiratory tract, resulting in little exposure to the immune system. The lung lesions, generally observed in young pigs, are characterized by a hyperplasia of the epithelial cells and an increased perivascular and peribronchiolar accumulation of mononuclear cells. Following *M. hyopneumoniae* infection, immune reactions are observed and resistance is induced in pigs. (Thacker, Anim Health Res Rev. 2004 December; 5(2):317-20 and Kobisch & Friis, Rev Sci Tech. 1996 December; 15(4):1569-605). Clinical symptoms and lesion development are the result of the pathogenic capacity of *M. hyopneumoniae* and the defense reactions in the lung. The economic relevance of pneumonia is influenced to a large extent by common secondary infections which follow an initial *M. hyopneumoniae* infection. Different tests for the diagnosis of pneumonia in individual pigs and in groups are available. Treatment and control are not simple since enzootic pneumonia is a multi-factorial disease (Maes et al., Vet Q. 1996, 18(3):104-9).

*M. hyopneumoniae* is also associated with porcine respiratory disease complex (PRDC), a multifactorial respiratory syndrome that includes several respiratory pathogens. The pathogens most commonly isolated from pigs with clinical signs of PRDC either infect the cells of the immune system or induce significant immunopathology. Thus, porcine reproductive and respiratory syndrome virus (PRRSV) and *M. hyopneumoniae*, the two most common pathogens associated with PRDC, alter the ability of the respiratory immune system to respond to their presence and the presence of other pathogens. By changing the respiratory immune system, these two common pathogens increase the susceptibility to the many other pathogens associated with PRDC (Thacker, Vet Clin North Am Food Anim Pract. 2001, 17(3):551-65).

The majority of known vaccines against *M. hyopneumoniae* have been based on adjuvanted inactivated whole cell preparations of *M. hyopneumoniae*. Commercial sources include RESPIFEND (Fort Dodge, American Home Products), HYORESP (Merial Ltd) or SPRINTVAC (MERIAL Ltd), M+PAC (Schering Plough), PROSYSTEM M (Intervet), INGELVAC M (Boehringer), RESPISURE (Pfizer Inc.), and STELLAMUNE *Mycoplasma* (Pfizer Inc.).

Porcine reproductive and respiratory syndrome virus (PRRSV) is a virus that causes the porcine reproductive and respiratory syndrome (PRRS), also known as blue-ear pig disease. This economically important, panzootic disease causes reproductive failure in breeding stock and respiratory tract illness in young pigs. Clinical signs of PRRS include reproductive failure in sows such as abortions and giving birth to stillborn or mummified fetuses, and cyanosis of the ear and vulva. PRRSV is a small, enveloped RNA virus. It contains a single-stranded, positive-sense, RNA genome with a size of approximately 15 kilobases. The genome contains ten open reading frames (Meulenberg et al., Virology. 1993, 192(1):62-72, Lee and Yoo, J Gen Virol. 2005, 86(11):3091-6; Johnson et al., J of Gen Virol. 2011, 92(5), pp. 1107-1116).

US patent application US 20130266603 relates to a trivalent immunogenic composition including a soluble portion of a *Mycoplasma hyopneumoniae* (*M. hyo*) whole cell preparation, a porcine circovirus type 2 (PCV2) antigen, and a PRRS virus antigen.

The prevalence of several infectious diseases of swine over the past several years have made it necessary to develop adapted multivalent vaccines and accompanying vaccination schedules. These schedules include the vaccination of pigs prior to maturity, which present logistical difficulties, i.e. the high number of pigs to vaccinate. Another practical problem is the interference when multiple vaccines are co-administered in an animal to treat several infectious diseases. In vaccinology and immunology this is the well-known and unpredictable phenomenon called "efficacy interference." In co-administration of vaccines (e.g., when two or more vaccines are administered together, either mixed together in the same formulation or in sequential administrations such as a primo- and boost administration as in the instant invention), the two vaccines can interfere. This phenomenon was first noted in the trivalent Sabin polio vaccine, where the amount of serotype 2 virus in the vaccine had to be reduced to stop it from interfering with the "take" of the serotype 1 and 3 viruses in the vaccine.

Infectious agents of swine, especially viruses, not only profoundly affect the farming industry, but pose potential public health risks to humans. Therefore, the development of preventions of PMWS or PCVAD and vaccinations for PCV are essential.

There is also a need for a single vaccine for combating PCV2, *Mycoplasma hyopneumoniae* (*M hyo*), and porcine reproductive and respiratory syndrome virus (PRRSV) multiple infections. Such a vaccine would eliminate the need for multiple dosing and thereby significantly decrease the costs and labor associated with the worldwide massive vaccination of swine herds. There remains a need for a multivalent vaccine that is efficacious and effective, easy to be administered to a large number of animals and cost effective.

SUMMARY OF THE INVENTION

The present invention provides a polyvalent *M hyo* composition or vaccine comprising: i) an *M hyo* antigen, and ii) at least one of: a PCV2 antigen, a PRRSV antigen, or a combination thereof.

The present invention also provides a composition or vaccine comprising a modified-live PRRSV antigen and an inactivated PRRSV antigen.

The present invention showed surprising benefit of *M. hyopneumoniae* vaccination used in multivalent vaccines to protect animals against a variety of swine pathogens, increase the ability of pigs to gain weights and reduce death loss. The present invention also demonstrated surprisingly that when modified-live PRRSV antigen and inactivated PRRSV antigen were administered together, the animal death rate was reduced.

The present invention relates to a method of vaccinating an animal, or inducing an immunogenic or protective response in an animal, comprising at least one administration of the composition or vector of the present invention.

The present invention also provides a vaccination kit or set, which may comprise one or more vaccine vials containing an *M hyo* vaccine, a PCV2 vaccine, and a PRRS vaccine.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 6 is a table showing the SEQ ID NO assigned to each DNA and protein sequence.

FIGS. 7A-7C depict sequence alignments and phylogenic tree.

DETAILED DESCRIPTION

Figure 1:
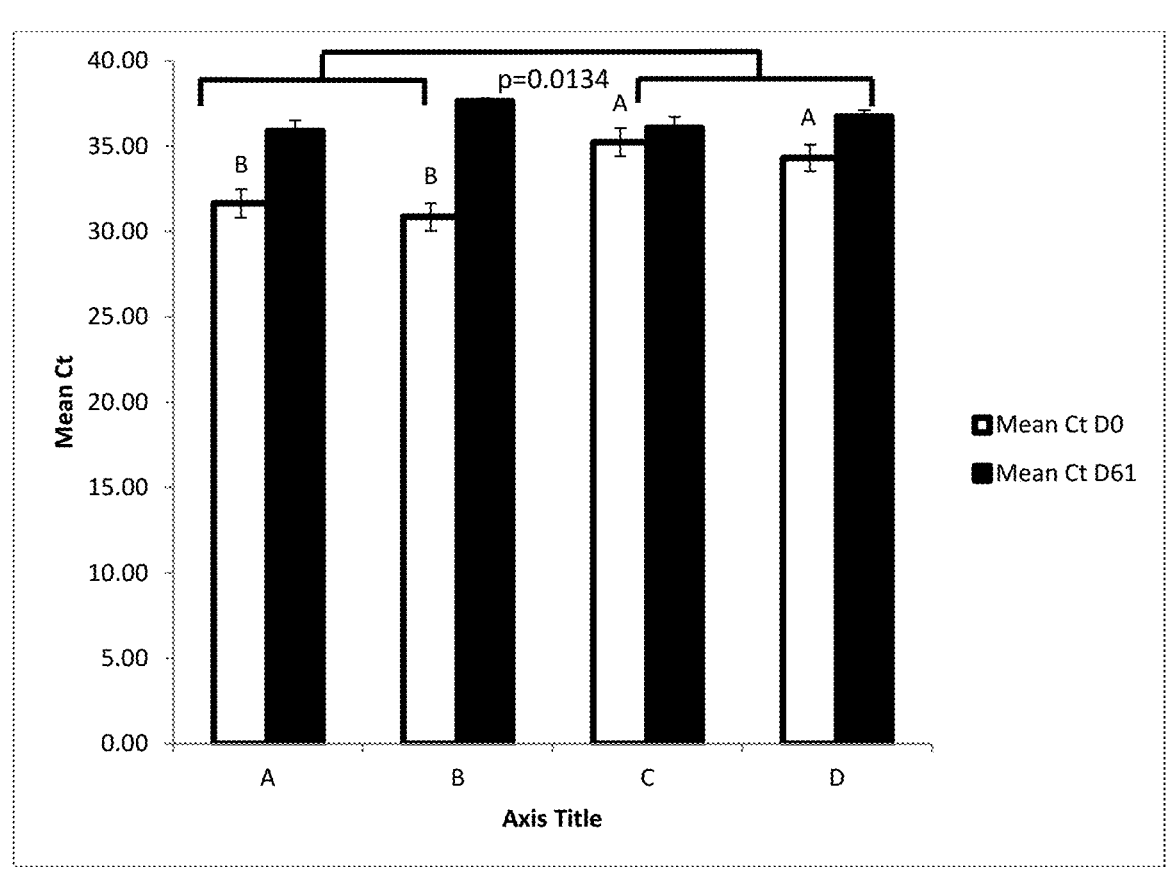
FIG. 1 depicts the qPCR performed on serum drawn on the first day of the study.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle, buffalos), swine (e.g., pig), ovine (e.g., sheep), caprine (e.g., goats), camelids (e.g., lamas), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

As used herein, the term "pig" or "piglet" means an animal of porcine origin, while "sow" refers to a female of reproductive age and capability.

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; transcription terminators (in general the terminator is located within approximately 50 nucleotides downstream of the stop codon of the coding sequence or gene). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers to a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an antigen, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or lowered pathogen loads in the infected host.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, subunits (proteins/antigens), DNA plasmids, or a mixture thereof.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with thimerosal, formalin, (betapropio-lactone) or BEI (binary ethylenimine)), sonication, radiation, heat or any other convention means sufficient to prevent replication or growth of the organism while maintaining its immunogenicity.

The PCV2 composition or vaccine may comprise a whole or partial cell preparation and/or the supernatant, such as killed virions or modified live preparation, a subunit vaccine, such as a subunit vaccine which may comprise one or more PCV2 derived polypeptides or proteins. The PCV2 composition or vaccine may comprise an inactivated virus.

The PCV2 may be any PCV2 strains disclosed in U.S. Pat. Nos. 6,368,601, 6,391,314, 6,660,272, 7,122,192, 7,144, 698, 7,192,594, 7,504,206, 7,741,039, 7,833,783, 7,803,613, 7,803,926, 7,211,379, 6,517,843. The PCV2 may be the strains Imp. 1008, Imp.1010, Imp999, Imp.1011-48285, Imp.1011-48121, Imp.1103, Imp.1121 as disclosed in U.S. Pat. Nos. 7,211,379 and 7,122,192. The PCV2 strain may be the strain Imp.1010 (CIRCOVAC©).

The PCV2 derived polypeptides or proteins may be those of PCV2 ORF2. The term "ORF2" as sued herein refers to circovirus antigens expressed from the open-reading frame ORF2 (as designated by Meehan et al. (1998) J. Gen. Virol. 78:221-227). ORF2 is believed to be a polypeptide contributing to the viral capsid. Thirteen open reading frames (ORFs) have been identified in the PCV2 genome. Further description of the PCV2 ORF2 may be found in U.S. Pat. Nos. 6,368,601, 6,391,314, 6,660,272, 7,122,192, 7,144, 698, 7,192,594, 7,504,206, 7,741,039, 7,833,783, 7,803,613, 7,803,926, 7,211,379, 6,517,843, 6,943,152, 6,217,883, 6,953,581, 6,497,883, 7,109,025.

The PCV2 composition or vaccine may further comprise an additional antigen derived from *Mycoplasma hyopneu-moniae* (*M hyo*), or porcine reproductive and respiratory syndrome virus (PRRSV), or a combination thereof. The antigen derived from *M hyo* or PRRSV may be a whole organism, killed, attenuated or live; a subunit or portion of an organism; a recombinant vector containing an insert encoding an antigen with immunogenic properties; a chimeric recombinant vector; a polypeptide, an antigen, or any combination thereof.

The inactivated pathogen or organism can be concentrated by conventional concentration techniques, in particular by ultrafiltration, and/or purified by conventional purification means, in particular using chromatography techniques including, but not limited to, gel-filtration or by ultrafiltration. As used herein, the term "immunogenicity" means capable of producing an immune response in a host animal against an antigen or antigens. This immune response forms the basis of the protective immunity elicited by a vaccine against a specific infectious organism.

The composition or vaccine of the present invention may comprise subunit vaccines having purified PCV2, *M hyo-pneumoniae* or PRRSV immunogenic proteins, polypeptides, antigens and immunogenic fragments of such proteins and polypeptides. Such proteins and polypeptides can be prepared using techniques known in the art. For example, the antigens or proteins may be produced in prokaryotes or eukaryotes. The prokaryotes contemplated in the present invention may include *Avibacterium, Brucella, Escherichia coli, Haemophilus* (e.g., *Haemophilus suis*), *Salmonella* (e.g., *Salmonella enteridis, Salmonella typhimurium, Salmonella infantis*), *Shigella, Pasteurella,* and *Rimeirella*. In prokaryotic systems, a number of expression vectors may be selected. Such vectors include, but are not limited to, the multifunctional *E. coli* cloning and expression vectors such as PBLUESCRIPT (Stratagene); pET vectors (Novagen); piN vectors (Van Heeke & Schuster, J. Biol. Chem. 264: 5503-5509 (1989)); and the like; PGEX Vectors (Promega, Madison, Wis.); In eukaryotic systems, the cell lines may be yeast (such as *Saccharomyces cerevisiae, Pichia pastoris*), baculovirus cells (such as Sf9, Sf21, Tn5B1-4, and S2), mammalian cells, plant cells (such as duckweed and microalgae). The expression vectors of eukaryotic systems include, but are not limited to, pVR1020 or pVT1012 vectors (Vical Inc., San Diego, CA), PichiaPink Vector (Invitrogen, CA, USA), pFasBac TOPO vector (Invitrogen).

Further, methods which are well known to those skilled in the art can be used to determine protein purity or homogeneity, such as polyacrylamide gel electrophoresis of a sample, followed by visualizing a single polypeptide band on a staining gel. Higher resolution may be determined using HPLC or other similar methods well known in the art. In a specific embodiment, the composition or vaccine comprises at least one protein of *M. hyopneumoniae* such as, but not limited to, P46, P65, P97, P102, P70, P50 and P44. For a sequence of the *M. hyopneumoniae* genome, reference is made to Minion et al., J Bacteriol. 2004 November; 186 (21):7123-33. In another specific embodiment, the composition or vaccine comprises at least one protein of PRRSV, such as, but not limited to, E, ORF3 and M.

In other embodiments, the composition or vaccine of the present invention comprises a *M. hyopneumoniae* bacterin (inactivated whole or partial cell), or modified live *M. hyopneumoniae*, or a *M. hyopneumoniae* protein or polypeptide or immunogenic fragment thereof. The *M hyo* bacterin may be the inactivated bacterin contained in MAIN-SAIL© (ProtaTek International, Inc., Saint Paul, MN). The *M hyo* bacterin may be the inactivated bacterin contained in SPRINTVAC©.

The *M hyo* composition or vaccine may further comprise an additional antigen derived from PCV2, or porcine reproductive and respiratory syndrome virus (PRRSV), or a combination thereof.

In other embodiments, the composition or vaccine of the present invention comprises a PRRSV (inactivated whole or partial cell), or modified live PRRSV, or a PRRSV protein or polypeptide, or a combination thereof. The composition or vaccine of the present invention may comprise a modified-live PRRSV and an inactivated PRRSV. The PRRSV may be any North American PRRSV or European PRRSV. The North American PRRSV may include, but is not limited to, ATCC VR-2332 strain (Collins et al., 1992, J Vet Diagn Invest 4:117-126), 807/94 strain (Canada), MN-1b strain (Kwang, J. et al., 1994, J, Vet. Diagn. Invest. 6:293-296), VR 2385 strain (Meng, X.-J et al., 1994, J. Gen. Virol. 75:1795-1801), the Quebec LAF-exp91 strain (Mardassi, H. et al., 1995, Arch. Virol. 140:1405-1418). The European PRRSV may include, but is not limited to, Olot strain (Spain), the Lelystad and 110 strains (The Netherlands), the PROGRES-SIS® strain (Merial Limited registered product). The PRRSV may be modified-live PRRS strain contained in INGELVAC PRRS® MLV vaccine (Boehringer Ingelheim). The PRRSV may also include strains isolated in Asia and South America.

In one embodiment, the present invention encompasses an attenuated live or inactivated/killed PRRS composition or vaccine.

In one embodiment, the present invention encompasses a novel inactivated/killed PRRSV composition or vaccine. The PRRSV strains are the PRRSV serotype newly identified in the USA. The inactivation may be the chemical inactivation that produces enumerable structural changes, including for example, formation of new chemical bonds via chemical crosslinking, irreversible chemical alteration of the nucleic acid and protein coat.

One embodiment of the invention provides the genomic DNA and gene sequences, and encoded protein sequences of PRRSV strains.

In another embodiment, the invention provides the sequences for ORF5 (also known as glycoprotein 5—GP5) proteins or antigens of PRRSV. In one aspect of the embodiment, the ORF5 proteins of PRRSV have the polypeptide sequence as set forth in SEQ ID NO:2, 3, 4, 5, 6, 7, 8, or 9. In another aspect, the ORF5 proteins have at least 70%, 75%, 80%, 85%, 90%, 95%, 96%, 97%, 98%, 99%, 99.1%. 99.2%, 99.3%, 99.4%, 99.5%, 99.6%, 99.7%, 99.8% or 99.9% sequence identity to a polypeptide having the sequence as set forth in SEQ ID NO:2, 3, 4, 5, 6, 7, 8, or 9. In yet another aspect, the ORF5 proteins are encoded by the polynucleotides having at least 70%, 75%, 80%, 85%, 90%, 95%, 96%, 97%, 98%, 99%, 99.1%. 99.2%, 99.3%, 99.4%, 99.5%, 99.6%, 99.7%, 99.8% or 99.9% sequence identity to a polynucleotide having the sequence as set forth in SEQ ID NO:1.

The invention further encompasses recombinant PRRSV antigens. The recombinant PRRSV antigens may include, but are not limited to, the recombinant PRRSV avipox viral vector (WO20030003112), the PRRSV plasmid vector (U.S. Pat. No. 6,576,243), the modified PRRSV (WO2006129139), the chimeric or recombinant proteins of PRRSV (EP1882478, EP0952219), the chimeric PRRSV (WO2008153572; U.S. Pat. No. 7,666,585; CN101603035; Res Vet Sci. 2013, 95(2):742-51), and genetically modified PRRSV (U.S. Pat. No. 6,841,364).

In another embodiment, the present invention contemplates preparation and isolation of a progeny or descendant of the PRRSV. The invention therefore extends to PRRSV strains which are derived from the PRRSV strains through propagation or multiplication in an identical or divergent form, in particular descendants which possess the essential characteristics of the deposited strains. Upon continued propagation, the strains may acquire mutations most of which will not alter the properties of these strains significantly. The progeny or descendant may comprise a polynucleotide encoding an ORF5 protein having at least 91% sequence identity to the sequence as set forth in SEQ ID NO:2, 3, 4, 5, 6, 7, 8, or 9, or a polynucleotide encoding an ORF5 protein having the sequence as set forth in SEQ ID NO:1.

The invention further encompasses at least one PCV2, *M. hyopneumoniae*, or PRRSV antigen contained in a vector molecule or an expression vector and operably linked to a promoter element and optionally to an enhancer.

A "vector" refers to a recombinant DNA or RNA plasmid or virus (viral vector) that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors and viral vectors.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

The present invention encompasses a vector expressing PCV2, *M. hyopneumoniae*, or PRRSV antigen or variants or analogues or fragments. Elements for the expression of the antigens are advantageously present in an inventive vector. At a minimum, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. a PCV2 antigen, or an *M. hyopneumoniae* antigen, or a PRRSV antigen, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

In one embodiment, the invention provides for the administration of a therapeutically effective amount of a formulation or composition for the delivery and expression of a PCV2, *M. hyopneumoniae*, or PRRSV antigen in a target cell. Determination of the therapeutically effective amount is routine experimentation for one of ordinary skill in the art.

The pharmaceutically or veterinarily acceptable carriers, adjuvants, vehicles, or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier, adjuvant, vehicle, or excipients that can be used for methods of this invention include, but are not limited to, poly-(L-glutamate) or polyvinylpyrrolidone. The pharmaceutically or veterinarily acceptable carrier, adjuvant, vehicle, or excipients may be any compound or combination of compounds facilitating the administration of the vector (or protein expressed from an inventive vector in vitro); the carrier, vehicle, adjuvant, or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121. Some of the emulsions, such as TS6, TS7, TS8 and TS9 emulsions, are described in U.S. Pat. Nos. 7,608,279 and 7,371,395.

In one embodiment, the adjuvant may include LR3 and LR4 (U.S. Pat. No. 7,691,368), TSAP (US20110129494), TRIGEN™ (Newport Labs), synthetic dsRNAs (e.g. poly-IC, poly-ICLC [HILTONOL®]), and MONTANIDE™ adjuvants (W/O, W/O/W, O/W, IMS and Gel; all produced by SEPPIC).

In a specific embodiment, the pharmaceutical and/or therapeutic compositions and/or formulations according to the invention comprise or consist essentially of or consist of an effective quantity to elicit a therapeutic response of one or more antigens as discussed herein; and, an effective quantity can be determined from this disclosure, including the documents incorporated herein, and the knowledge in the art, without undue experimentation.

The dose may include about $10^2$ to about $10^{20}$, about $10^3$ to about $10^{18}$, about $10^4$ to about $10^{16}$, about $10^5$ to about $10^{12}$ VLPs (viral like particles). The viral particles may be calculated based on any virus titration methods including, but not limited to, FFA (Focus Forming Assay) or FFU (Focus Forming Unit), $TCID_{50}$ (50% Tissue Culture Infective Dose), PFU (Plaque Forming Units), and $FAID_{50}$ (50% Fluorescent Antibody Infectious Dose). The dose volumes can be between about 0.1 and about 10 ml, advantageously between about 0.2 and about 5 ml.

In the case of M hyo bacterin vaccine, the composition or vaccine may contain from about $1 \times 10^6$ to about $5 \times 10^{10}$ colony forming units (CFU) per dose, about $1 \times 10^8$ to about $5 \times 10^{10}$ CFU/dose, and about $5 \times 10^8$ to about $5 \times 10^{10}$ CFU/dose.

The composition or vaccine may contain from about $10^{2.0}$ to about $10^{10.0}$ $TCID_{50}$ or PFU/dose, from about $10^{2.0}$ to about $10^{8.0}$ $TCID_{50}$ or PFU/dose, and from about $10^{2.0}$ to about $10^{6.5}$ $TCID_{50}$ or PFU/dose. The composition or vaccine may contain equivalent $TCID_{50}$ or PFU in the case of inactivated/killed composition or vaccine.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Biojector or Vitajet apparatus (Bioject, Oreg., USA)).

In one embodiment of the invention, a prime-boost regimen can be employed, which is comprised of at least one primary administration and at least one booster administration using at least one common polypeptide, antigen, epitope or immunogen. The immunological composition or vaccine used in primary administration is different in nature from those used as a booster. However, it is noted that the same composition can be used as the primary administration and the boost. This administration protocol is called "prime-boost". The prime-administration may comprise one or more administrations. Similarly, the boost administration may comprise one or more administrations.

The composition or vaccine is administered to a pig or weaning pig. A booster administration can be done if necessary around 2 to 8 weeks after the first administration. In another embodiment, the composition or vaccine is administered to a pig or sow so that piglets acquire passive immunity against PCV2, M. hyopneumoniae, and/or PRRSV infection from suckling colostrum and milk. A booster administration can also be repeated every 6-month or every year, especially for the pigs or sows.

Another object is a vaccination kit or set, comprising at least one vaccine vial containing an M hyo composition or vaccine, or M hyo multivalent composition or vaccine, or M hyo/PCV2 composition or vaccine, or PRRS composition or vaccine, or a combination thereof, operatively assembled to perform the administration of the vaccine to an animal of the swine family.

Such vaccination kit or set is able to elicit a safe and protective immune response against PCV2, M. hyopneumoniae, and/or PRRSV infection.

The invention will now be further described by way of the following non-limiting examples.

EXAMPLES

Example 1 Efficacy Study of M Hyo Multivalent Vaccines and PRRSV Vaccines

Porcine Reproductive and Respiratory Syndrome Virus (PRRSV) and Mycoplasma hyopneumoniae are two of the most commonly isolated pathogens of the porcine respiratory disease complex. In pig flows where both of these pathogens are present infection with M. hyopneumoniae often predisposes pigs to infection with PRRSV. (1) In an in vitro model, increased levels of inflammatory cytokines are induced by coinfection, which may continuously draw more macrophages to the site of infection in the lung and prolong the infection. (2) If this translates to the field, pneumonia induced by coinfection may result in a longer duration of PRRSV induced pneumonia than is observed when the infection is potentiated by the virus by itself. PRRSV strains currently circulating in the field possess a high level of genetic heterogeneity such that commercial vaccines are often unable to provide protection against heterologous strains of virus. (3) Recently, a new strain of PRRSV exhibiting a 1-7-4 RFLP pattern has been increasing in prevalence within the United States. (4) Preliminary reports from the field have described a lack of protection obtained with commercial vaccines against this virulent new strain. When M. hyopneumoniae is present on a farm, the outcome of infection with this virus may be worsened. New vaccination strategies are needed that can combat the combined pathologies associated with these two pathogens, particularly after weaning when pigs become most susceptible to infection.

In this study, a field study was performed in which four different vaccination strategies were tested to determine whether they would be able to enhance weight gain from weaning to 12 weeks of age.

PRRSV strains were isolated from 28 day pigs serum from an infected nursery showing clinical signs of PRRS. RNA was extracted and sequenced. Propagated PRRS viruses were inactivated by a chemical reaction using BEI (binary ethylenimine). Formaldehyde or BPL (betapropio-lactone) may also be used to inactivate the PRRS viruses. One hundred and sixty PRRS positive pigs were separated into four groups. The pigs were a mixture of males and females. The pigs were about 21-day old and weighed about eighteen pounds on average.

TABLE 1

Treatment groups

| Group | Treatment | n |
|---|---|---|
| A | Commercial PRRSV MLV Vaccine[1], Circovac PCV2 Vaccine[2], inactivated autogenous PRRSV vaccine[3] | 40 |
| B | Commercial PRRSV MLV and Circovac PCV2 vaccine | 40 |
| C | Commercial PRRSV MLV, Circovac PCV2 Vaccine, MAINSAIL ® *Mycoplasma hyopneumoniae* vaccine[4], inactivated autogenous PRRSV vaccine | 40 |
| D | Commercial PRRSV MLV, Circovac PCV2 Vaccine, and MAINSAIL ® *Mycoplasma hyopneumoniae* vaccine | 40 |

Commercial PRRSV MLV Vaccine[1]: INGELVAC PRRS ® MLV vaccine (Boehringer Ingelheim), label dose.
Circovac PCV2 Vaccine[2]: PCV2 vaccine CIRCOVAC ® (inactivated vaccine commercialized by Merial Limited) containing PCV2 strain Imp.1010, 2 ml/dose.
inactivated autogenous PRRSV vaccine[3]: in TS6 adjuvant/emulsion (66.66% TS6 + 33.33% PRRSV harvest fluids) (TS6 as described in U.S. Pat. No. 7,608,279 and U.S. Pat. No. 7,371,395, and also in Table 3), 1 cc dose
MAINSAIL ® *Mycoplasma hyopneumoniae* vaccine[4]: inactivated M hyo bacterin vaccine (ProtaTek International, Inc., Saint Paul, MN), 1 ml/dose.

TABLE 2

Treatment Scheme

| Group | Treatment | Route | Volume | Frequency | Challenge |
|---|---|---|---|---|---|
| A | 1 dose Ingelvac PRRS ® MLV vaccine right side of the neck at weaning | IM | 0.5 mL MLV PRRS | One dose Ingelvac PRRS | Natural Exposure |
| | 1 dose Circovac vaccine right side of the neck at weaning | | 0.5 mL Circovac | One dose Circovac | |
| | 1 dose killed PRRS vaccine left side of the neck. 3 weeks later 2nd dose of killed PRRS vaccine on left side of neck | | 1.0 mL killed PRRS | Two doses Killed PRRS | |
| B | 1 dose Ingelvac PRRS ® MLV vaccine right side of the neck at weaning | IM | 0.5 mL MLV PRRS | One dose Ingelvac PRRS | Natural Exposure |
| | 1 dose Circovac vaccine right side of the neck at weaning | | 0.5 mL Circovac | One dose Circovac | |
| C | 1 dose Ingelvac PRRS ® MLV vaccine right side of the neck at weaning | IM | 0.5 mL MLV PRRS | One dose Ingelvac PRRS | Natural Exposure |
| | 1 dose Circovac vaccine right side of the neck at weaning | | 0.5 mL Circovac | One dose Circovac | |
| | 1 dose killed PRRS vaccine left side of the neck. 3 weeks later 2nd dose of killed PRRS vaccine on left side of neck | | 1.0 mL killed PRRS | Two doses Killed PRRS | |
| | 1 dose Mainsail vaccine right side of the neck at weaning | | 1 mL Mainsail | One dose Mainsail | |
| D | 1 dose Ingelvac PRRS ® MLV vaccine right side of the neck at weaning | IM | 0.5 mL MLV PRRS | One dose Ingelvac PRRS | Natural Exposure |
| | 1 dose Circovac vaccine right side of the neck at weaning | | 0.5 mL Circovac | One dose Circovac | |
| | 1 dose Mainsail vaccine right side of the neck at weaning | | 1 mL Mainsail | One dose Mainsail | |

TABLE 3

TS6 emulsion (premulsion described in U.S. Pat. No. 7,608,279 and U.S. Pat. No. 7,371,395)

| Oily phase (120 ml) | |
|---|---|
| Sorbitan monooleate (SPAN 80 ®) | 1.8% w/v |
| Sorbitan trioleate (20 OE) (TWEEN 85 ®) | 10.2% w/v |
| Paraffin oil (MARCOL 82 ®) | 88% v/v |
| Aqueous phase (120 ml) | |
| 20% (w/v) solution of sorbitan monooleate (20 OE) (TWEEN 80 ® | 11.25% w/v |
| Phosphate disodic and monopotassic 0.02M isotonic buffer (pH7.8) | 85.75% v/v |
| Sodium mercurothiolate (Thionersal ®) 1% in water | 1.5% v/v |

Figure 2:
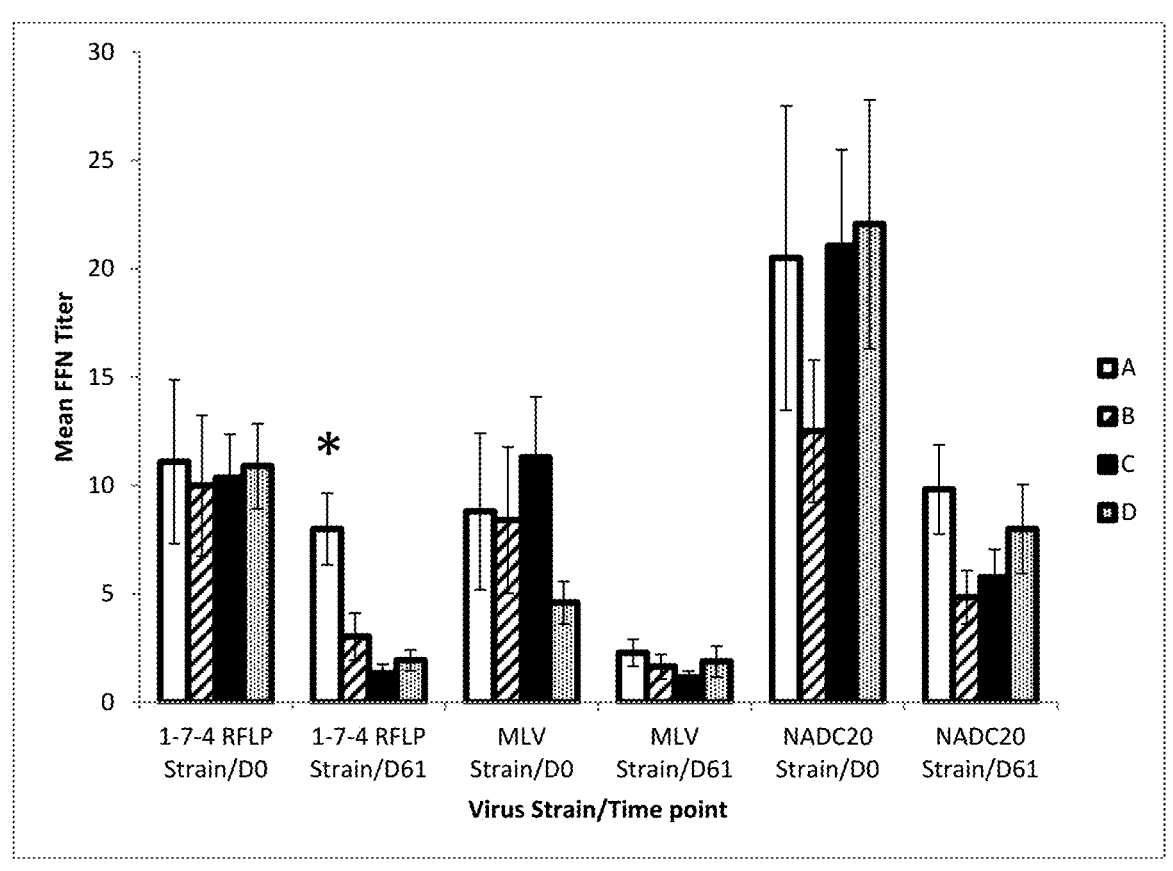
FIG. 2 depicts FFN Titers from serum drawn on days 0 and 21.
Figure 3:
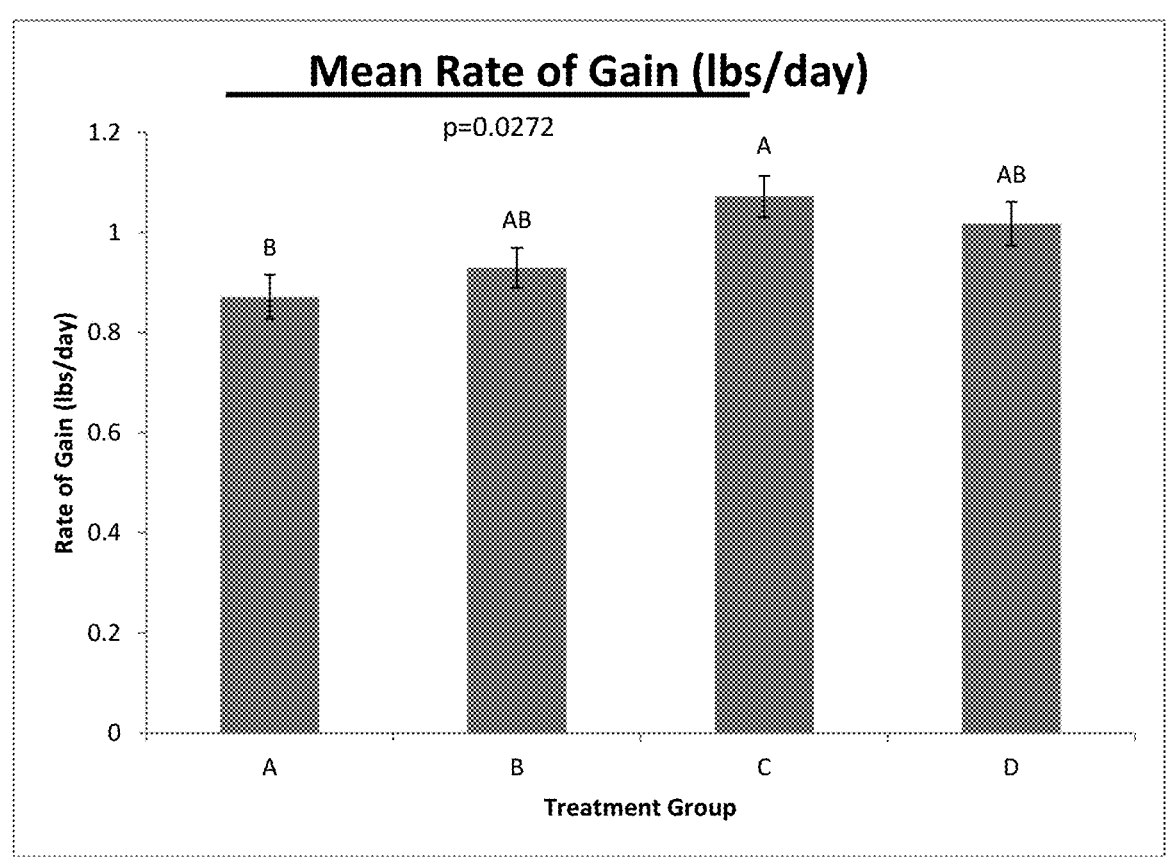
FIG. 3 depicts the mean rate of weight gain among groups.
Figure 4:
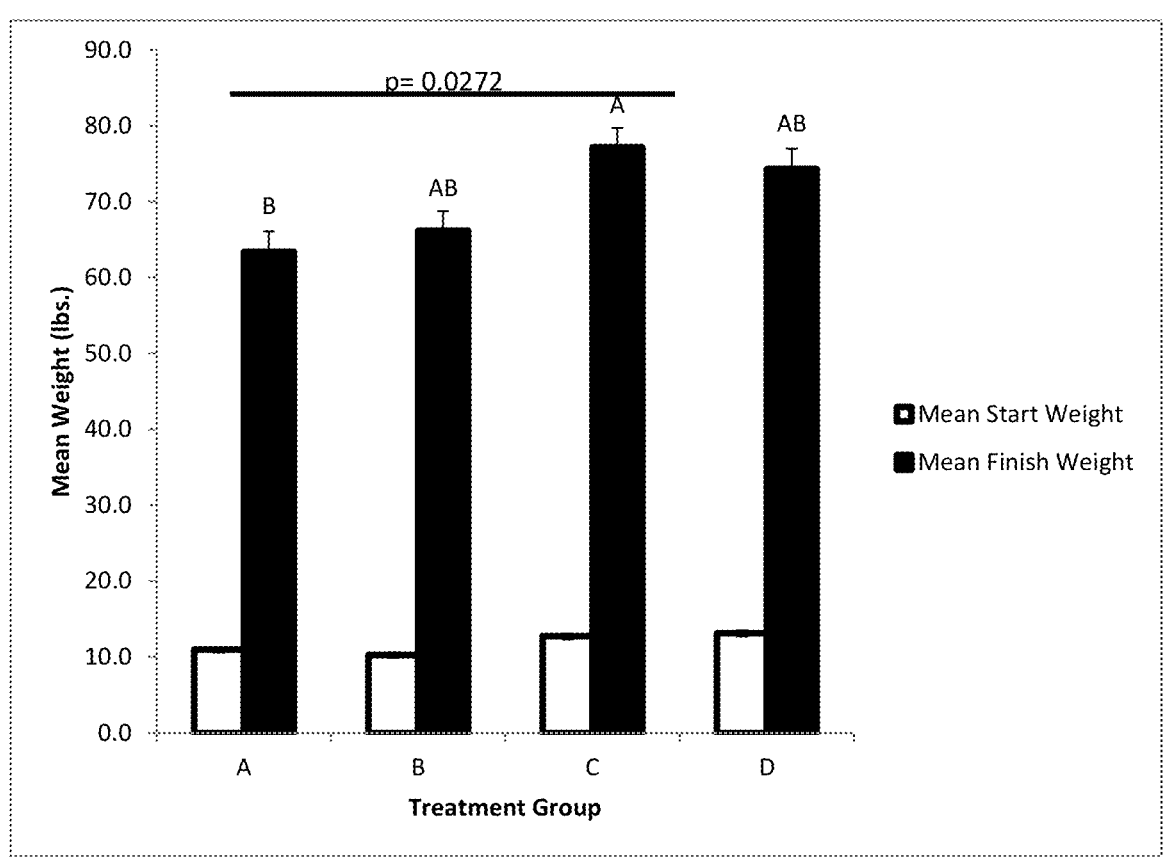
FIG. 4 depicts mean weight of groups at days 0 and 61 of the study.
Figure 5:
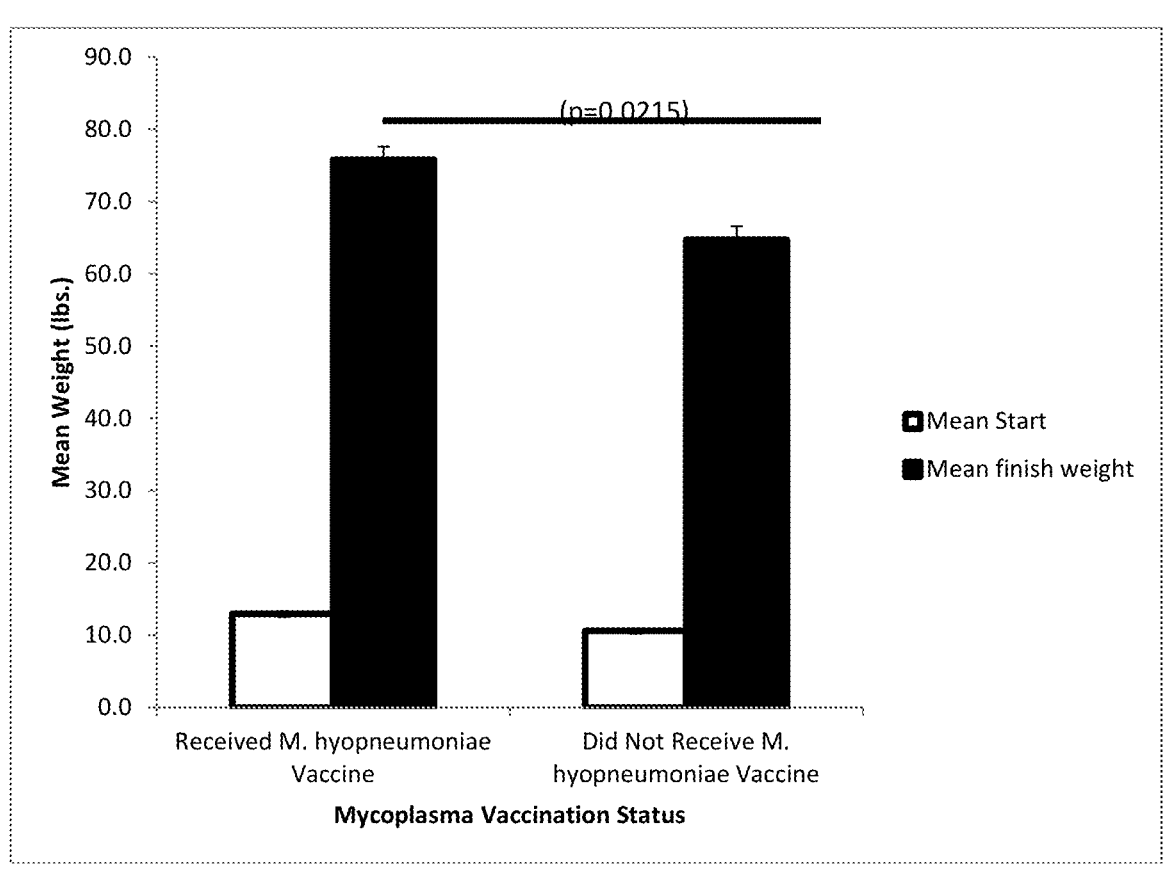
FIG. 5 depicts comparison of finishing weights based on *Mycoplasma* Vaccination Status.
Figure 7C:
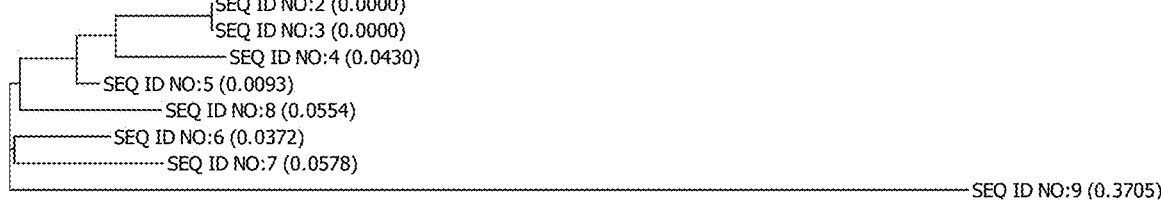

Animals were followed for 61 days and weighed on days 0 and 61. Serum samples were also drawn at both time points and were assessed for the presence of PRRSV by qPCR (FIG. 1) and for neutralizing antibody titer using a Fluorescent Focus Neutralization assay (FFN). Neutralizing antibody titers were measured against both the strains used in vaccination treatments as well as a heterologous strain, NADC20 (FIG. 2). Weight gain was assessed between all groups using a two-way ANOVA ($\alpha=0.05$) to determine whether the factors, start weight and treatment group, had a statistically significant impact on the outcome variable, finish weight (FIG. 3). Groups were then ranked using Student's t-test ($\alpha=0.05$) in order to visualize statistically significant differences between groups (FIG. 4). Pigs were similarly assessed to determine whether vaccination with *M. hyopneumoniae* had a statistically significant impact on finish weight irrespective of the other components of the treatment given (FIG. 5).

The results of the study were complicated by the fact that animals in treatment groups A and B were significantly lighter than animals in groups C and D at the beginning of the study. Based on the qPCR results from serum drawn at the beginning of the study it seems that this difference may have been due to a more severe PRRSV infection in groups A and B. This evidence is further supported by the results of our FFN testing which demonstrated a statistically significant difference in neutralizing antibody titer against the 1-7-4 RFLP virus for pigs in group A at the end of the study. It seems likely that these pigs experienced a more severe challenge with this virus prior to vaccination. The inactivated vaccine delivered at day 0 might have served as a booster vaccination following this challenge. This may have resulted in enhanced neutralizing antibody titers at the end of the study in comparison to the other groups that either did not receive the vaccine, or were not as severely infected at the beginning of the study.

Another study was done to assess the effect of inactivated autogenous PRRSV vaccine when used with PRRSV MLV at the same time. Results showed a 2-5% improvement in death loss when using killed PRRS with MLV (Table 4).

TABLE 4

Effect of inactivated PRRS vaccine

| Group | Death loss improvement |
|---|---|
| A: Control (1 dose Ingelvac PRRS ® MLV vaccine) | — |
| B: 1 dose Ingelvac PRRS ® MLV vaccine + 1 dose inactivated autogenous PRRSV vaccine | 2.5% |
| C: 1 dose Ingelvac PRRS ® MLV vaccine + 1 dose inactivated autogenous PRRSV vaccine + 1 dose MAINSAIL ® *Mycoplasma hyopneumoniae* vaccine | 5.0% |

When comparing treatments that resulted in a significant increase in weight gained by the end of the study, the *M. hyopneumoniae* vaccination clearly stood out as a factor that increased the ability of the pigs to gain weight. Pigs that received an *M. hyopneumoniae* vaccination finished the study an average of 11 pounds heavier than pigs that did not receive this treatment and the death loss improvement is 3.7% in the *M. hyopneumoniae* vaccinated groups. Thus, a significant economic advantage can be assigned to *M. hyopneumoniae* vaccination. The results demonstrate a significant weight advantage for animals that received an *M. hyopneumoniae* vaccination.

The data indicate that the benefit of *M. hyopneumoniae* vaccination is currently underestimated in the field. The data also indicate that the administration of inactivated PRRSV vaccine with PRRSV MLV reduced the death rate. Further, the results show that no interference was observed when *M hyo* vaccine was mixed with PCV2 and PRRSV vaccines.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A vaccine for vaccination of a swine against a swine disease, comprising:
   a *Mycoplasma* hyopneumoniae (*M hyo*) antigen;
   a killed Porcine Reproductive and Respiratory Syndrome Virus (PRRSV) antigen; and
   a modified-live PRRSV antigen.

2. The vaccine of claim 1, wherein the *M hyo* antigen is an inactivated *M hyo*.

3. The vaccine of claim 1, wherein the killed PRRSV antigen comprises a polynucleotide encoding an ORF5 protein having at least 99.6% sequence identity to the sequence as set forth in SEQ ID NO:2, 3, 4, 5, 6, 7, 8, or 9.

4. The vaccine of claim 1, wherein the vaccine further comprises one or more pharmaceutically or veterinarily acceptable carrier, adjuvant, vehicle, or excipient.

5. A vaccination kit or set comprising one or more vaccine vials containing the vaccine of claim 1.

6. A vaccine for vaccination of a swine against a swine disease, comprising:
   a killed Porcine Reproductive and Respiratory Syndrome Virus (PRRSV) antigen; and
   a modified-live PRRSV antigen.

7. The vaccine of claim 6, further comprising a Mycoplasma hyopneumoniae (M hyo) antigen.

\* \* \* \* \*